US006297733B1

(12) United States Patent
Park

(10) Patent No.: US 6,297,733 B1
(45) Date of Patent: Oct. 2, 2001

(54) STABLE, RELIABLE CAPACITIVE OIL DETERIORATION AND LEVEL SENSOR

(75) Inventor: Kyong M. Park, Westlake Village, CA (US)

(73) Assignee: Kavlico Corporation, Moorpark, CA (US)

( * ) Notice: Subject to any disclaimer, the term of this patent is extended or adjusted under 35 U.S.C. 154(b) by 0 days.

(21) Appl. No.: 09/710,588

(22) Filed: Nov. 10, 2000

(51) Int. Cl.[7] ........................................ B60Q 1/00
(52) U.S. Cl. ............... 340/450.3; 340/450; 340/450.1; 340/450.2; 340/451; 340/452
(58) Field of Search ................. 340/450.3, 450, 340/451, 450.2

(56) References Cited

U.S. PATENT DOCUMENTS 5,060,108 * 10/1991 Baker et al. ........................ 361/283
5,233,875 * 8/1993 Obermeier et al. ................. 73/718
5,329,819 * 7/1994 Park et al. ........................... 73/724
5,929,754 * 7/1999 Park et al. ......................... 340/439

* cited by examiner

Primary Examiner—Jeffery Hofsass
Assistant Examiner—Son Tang
(74) Attorney, Agent, or Firm—Oppenheimer Wolff & Donnelly, LLP

(57) ABSTRACT

A reliable capacitive oil deterioration and level sensor has a conductive housing member that includes a conductive shielding member defining a ground electrode, and a conductive inner member defining a measuring electrode. The shielding member protects the sensor from moving objects that could adversely affect its performance. The housing member is adapted to provide a fluidic connection between an oil container and a space between the ground electrode and the measuring electrode. The sensor also includes electronics adapted to employ this capacitor geometry to generate signals indicative of a degree of deterioration and a level of the oil within the gap. The electronics further include at least one isolating capacitor to eliminate a flow of current between the electrodes that may cause a build up of material on the two electrodes that define the capacitor. This build up of unwanted material may cause an undesirable effect in the sensor output signal.

20 Claims, 3 Drawing Sheets

STABLE, RELIABLE CAPACITIVE OIL DETERIORATION AND LEVEL SENSOR

RELATED APPLICATIONS

This application is related to U.S. patent application Ser. No. 08/984,584, now U.S. Pat. No. 5,929,754.

BACKGROUND OF THE INVENTION

1. Field of the Invention

The present invention relates to a multi-functional sensor and, more particularly, pertains to a design of a reliable capacitive oil deterioration and level sensor whose measurements are insensitive to changes in the operating environment of the sensor.

2. Description of the Related Art

One of the most important factors that contributes to the efficiency and durability of internal combustion engines is lubrication. As engine oil "breaks down" it is less effective in protecting an engine from damage caused by friction between engine parts. More specifically, the normal life span of motor oils is limited by thermal breakdown, additive depletion and carbon particulates that result from the combustion process.

The deterioration of engine oil is marked by a decrease in the viscosity of the oil. The dielectric constant of engine oil provides an indication of the oil's deterioration or lack thereof.

The dielectric constant of motor oil is typically between 1.6 and 3.2 depending upon its brand and age. For example, the dielectric constant of a particular brand of motor oil may increase from 2.19 to 3.2 after 400 hours of use in a particular internal combustion engine under certain operating conditions. Thus, it is desirable to have a means for indicating reliably when engine oil has deteriorated to the point where it should be changed.

Premature lubrication failure can also result from the presence of contaminants in the engine oil such as coolant (glycol ethylene), filel or water. The presence of these contaminants in motor oil is often indicative of a mechanical failure such as a damaged head gasket or a broken piston ring. Water and engine coolant have dielectric constants of approximately 87.5 and 37.0, respectively. The introduction of such contaminants into the engine oil significantly increases the dielectric constant of some of the fluid which circulates through the engine for the purpose of lubrication. Thus, it is also desirable to have a means for detecting the presence of these substances in engine oil.

The dielectric constant of oil is also influenced by the temperature of the oil and by the specific formulation of a given brand of oil. Thus, it is also desirable to provide a multi-functional sensor with a means for compensating for changes in the dielectric constant of oil resulting from these factors.

U.S. Pat. No. 5,929,754 of Dr. K. M. Park et al. discloses a high-sensitivity capacitive oil deterioration and level sensor that measures the dielectric constant of the liquid suspension. However, under certain circumstances, the output of this sensor has not been as stable as would be desired.

Accordingly, a principal object of the present invention is to increase the stability and reliability of sensors of the type disclosed in the above-identified patent.

SUMMARY OF THE INVENTION

It has been determined that the undesired variations in the output of the sensors of the type shown in the patent cited above may arise from (1) the presence of nearby moving objects such as a crankshaft or other metallic objects, and (2) current flow between the capacitive electrodes which may result in a build-up of a material on at least one of the electrodes.

Accordingly, a more specific object of the present invention is to include a protection mechanism for the high-sensitivity capacitive oil deterioration and level sensor, such that the presence of nearby moving parts do not affect the output from the sensor, thereby providing more reliable measurements.

Another specific object is to provide an isolation for the electrodes of the high-sensitivity capacitive oil deterioration and level sensor so as to eliminate unwanted flow of current between the electrodes, which can adversely affect the measurements from the sensor.

In accordance with a specific illustrative embodiment of the present invention, a reliable capacitive oil deterioration and level sensor includes an inner member (electrode), and a combined outer electrode and shielding member (hereupon referred to as a shield-electrode). The outer shield-electrode may also be a part of the housing of the sensor system, and this entire subassembly may be at ground potential. The sensor also preferably includes an electrical connector and associated electronics. The housing member may include a threaded outer surface adapted to be threaded into the oil pan of an internal combustion engine.

The outer shield-electrode has at least one port sized to allow oil within the oil pan to flow into and through a space between the outer shield-electrode and the inner electrode. The shield-electrode protects the sensor assembly from the effect of moving objects such as a crankshaft and/or metallic objects. The inner electrode includes a cylindrical portion with an outer surface defining a measuring electrode. The inner electrode is secured within the housing member by an insulating spacer such that the outer grounded shield-electrode, and the inner measuring electrode define an oil deterioration and level sensor variable capacitor. An electrical connector is adapted to provide an electrical interface to a processor.

The provided electronics within the housing member may include a reference capacitor. The reference capacitor can also be located external to the electronics. The electronics are electrically connected to the oil deterioration and level sensor capacitor, the reference capacitor, and the electrical connector. The electronics are adapted to generate an oil deterioration output signal and an oil level output signal employing the oil deterioration and level sensor capacitor and the reference capacitor and to provide signals to the electrical connector.

The electronics within the housing member contain additional isolating capacitors. The isolating capacitors have a magnitude at least several times greater than the capacitance of the variable and the reference capacitor. Preferably two isolating capacitors are used, one in series with each of the variable and reference capacitors on either side thereof. However, in some cases a single isolating capacitor between a common output point of the variable, fixed capacitors and ground may be effective. The isolating capacitors prevent any net flow of direct current between the two electrodes, and therefore avoid any build-up of material at either electrode, which might otherwise adversely change the sensor output.

DESCRIPTION OF THE DRAWINGS

Other objects, features and advantages of the invention will become readily apparent upon reference to the following detailed description when considered in conjunction with the accompanying drawings, in which like reference numerals designate like parts throughout the figures thereof, and wherein.

DETAILED DESCRIPTION OF THE PREFERRED EMBODIMENTS

Figure 1:
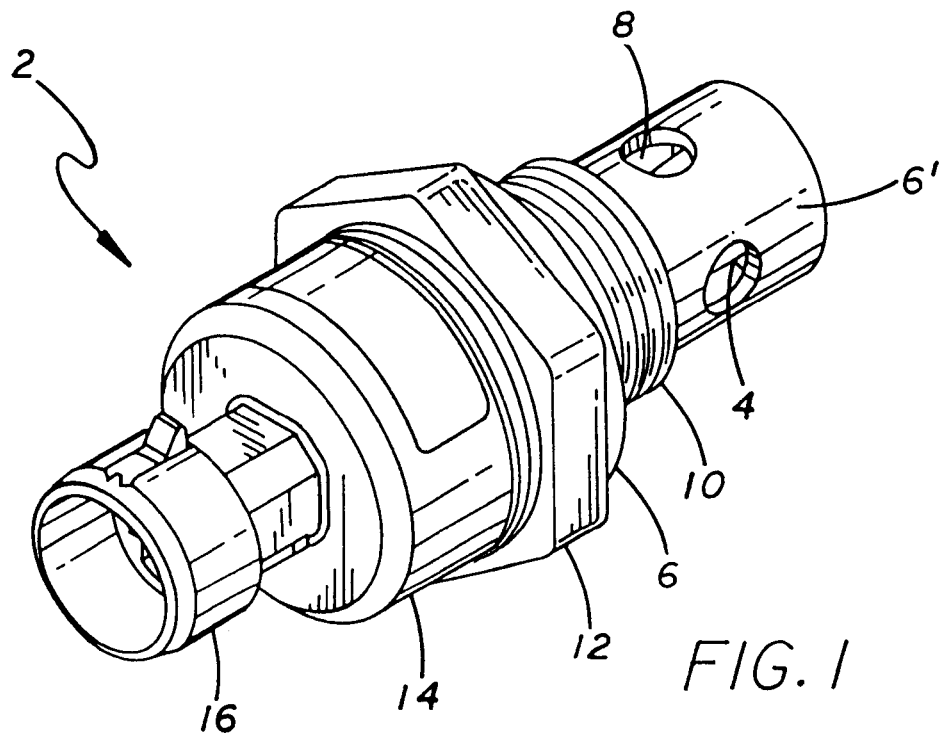
FIG. 1 is a perspective view of the reliable capacitive oil deterioration and level sensor assembly having a metallic shielding structure with fluid inlet ports illustrating aspects of the present invention.

FIG. 1 is a perspective view of a preferred exemplary embodiment of a reliable capacitive oil deterioration and level sensor 2. The sensor 2 includes a conductive housing member 6 with the outer shield-electrode 6', a conductive inner electrode 4, and an electrical connector structure 16 which are interfitted as shown. In a preferred embodiment, the shield-electrode 6' and the inner electrode 4 are cylindrical in form. The shield-electrode 6' has at least one inlet port 8 on the side, and an inlet port at the top (not shown) to allow fluid to enter and flow through a space between the shield-electrode 6' and the inner electrode 4. In the preferred embodiment, this space is cylindrical, when the shield-electrode 6' and the inner electrode 4 are cylindrical in shape. Additionally, the sensor assembly 2 may be designed with threads 10 and a hexagonal nut configuration on the housing 6, so as to allow an operator to rotatively insert and remove the sensor assembly 2 from a structure such as a fluid container (oil-pan in an internal combustion engine). The lower member 14 is made of plastic and has an electronic board with circuitry (not shown) to transform the measured capacitance into an output voltage.

Figure 3:
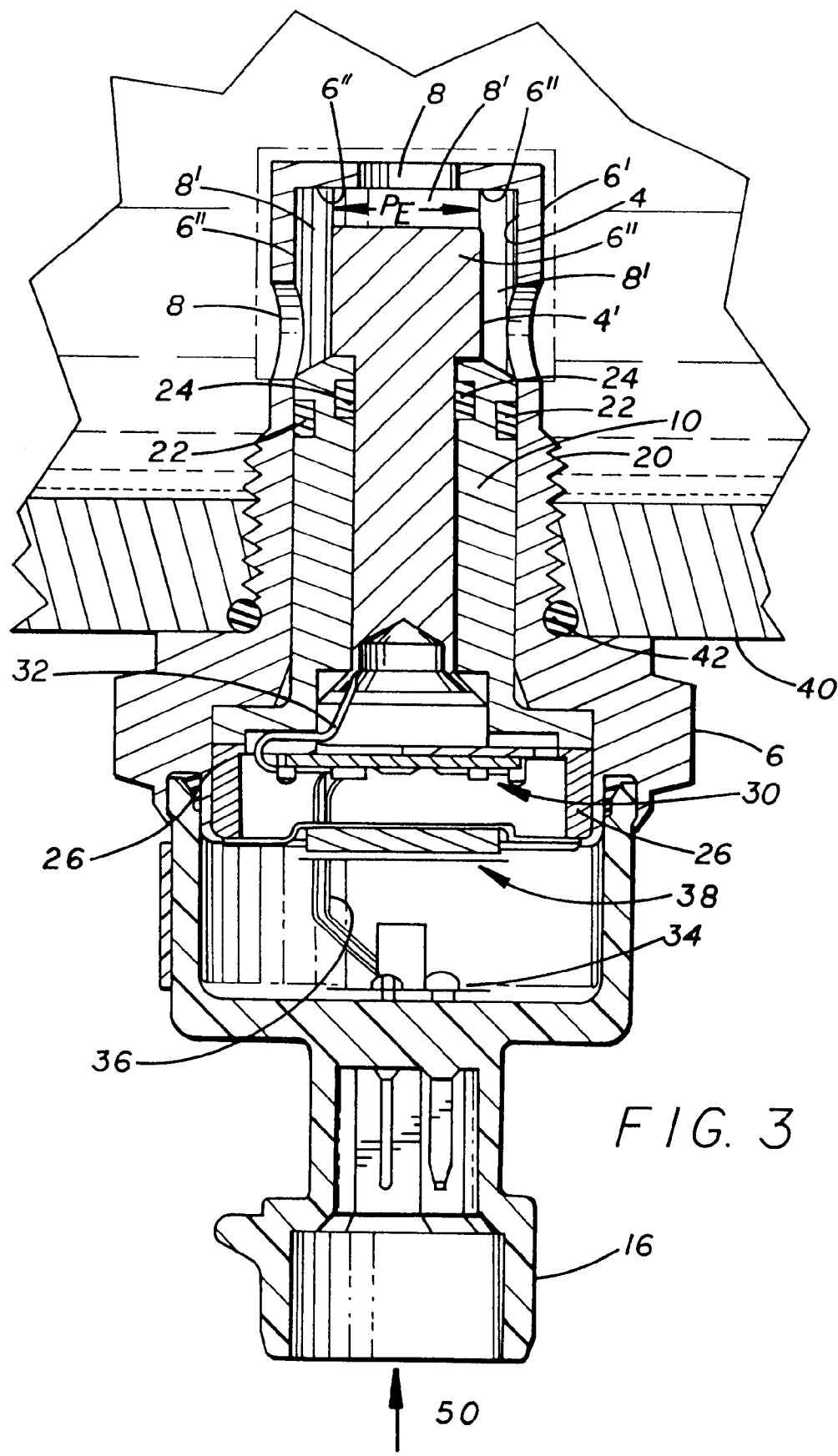
FIG. 3 is a cross sectional side view of the oil deterioration and level sensor assembly having a metallic shield with fluid inlet ports, and internally mounted electronics.

With reference to FIG. 3, in a preferred embodiment, the shield-electrode 6' includes an inner surface 6" which defines a ground electrode. The inner electrode 4 includes an outer surface 4' which defines a measuring electrode. The inner electrode 4 is secured within the housing member 6 such that the ground electrode 6" and the measuring electrode 4' define an oil deterioration and level sensor capacitor ($C_e$).

The housing member 6 also includes a threaded outer surface 10 which, in a preferred embodiment, is adapted to be threaded into an oil pan 40 of an internal combustion engine. The threaded surface may be made of a metal. The scope of the present invention additionally contemplates applications which do not involve combustion but where oil is still monitored for degradation, e.g., compressors, pumps, and gearboxes.

The housing member 6 also has an insulating spacer or insulator 20 housed inside. The insulating spacer 20 is designed and positioned in a such a way,as to support the inner electrode 4. In a preferred embodiment, the insulating spacer 20 engages the inner electrode 4, at a shoulder on the electrode. Gaskets 22 seal an interface between the insulating spacer 20 and the housing member 6, whereas gaskets 24 seal an interface between the insulating spacer 20 and the inner electrode 4.

The lower portion of the insulating spacer 20 is connected to a top portion of a support 26.

The lower edge of the housing member 6 is peened over the lower outer corner of support 26 to hold the assembly together.

The shield-electrode 6' is formed with at least one port 8 sized to allow oil within the oil container 40 to enter into the space 8' formed between the inner electrode 4 and the shield-electrode 6. In the illustrated preferred embodiment, there is another port 8 at the top of the shield-electrode 6'. The presence of the port at the top does not significantly interfere with the shielding function of the member 6' with respect to moving objects, thereby permitting reliable operation of the sensor.

Further with regard to the reliable oil deterioration and level sensor capacitor ($C_e$), the capacitance of the cylindrical capacitor is given by:

$$C_e = 2\pi \epsilon L / \log(D_e / D_G),$$

where:

$\epsilon$ is the dielectric constant of the oil within the gap 8';

L is the length of the inner electrode (see FIG. 3);

$D_e$ is the outside diameter of the cylindrical portion of the inner electrode 4; and $D_G$ is the inside diameter of the cylindrical portion of the shield-electrode 6'.

Electronics positioned within the housing member 6 include the oil deterioration and level sensor capacitor ($C_e$), a reference capacitor ($C_r$), and additional circuit elements which are preferably provided in an integrated circuit 30 (e.g., a hybrid integrated circuit).

The hybrid circuit 30 is positioned within the housing member 6 and is mounted on the support 26. A plurality of conductive leads 32 connect the electronics within the hybrid circuit 30 to the oil deterioration and level sensor capacitor ($C_e$), and the reference capacitor ($C_r$) situated in the hybrid circuitry. Specifically, lead 32 electrically connects the hybrid circuit 30 to the inner electrode 4.

The electrical connector structure 16 includes conductive terminals to provide power to the electronics and easy access to the output signals generated by the electronics. The terminals are electrically connected to the hybrid circuit 30 via a flexible strip 34, which includes wiring elements, and leads 36. A feed-through plate assembly 38 supports the flexible strip 34 and the leads 36. Additionally, the feed-through plate assembly 38, in turn, is secured to the housing member 6. The sensor 2 additionally includes a plurality of conventional o-ring gaskets 42 configured as shown.

As discussed above, the electronics are electrically connected to the oil deterioration and level sensor capacitor ($C_e$). As discussed below in greater detail, the electronics are adapted to employ the capacitor ($C_e$) to generate signals indicative of a degree of deterioration and a level of the oil within the gap.

Figure 4:
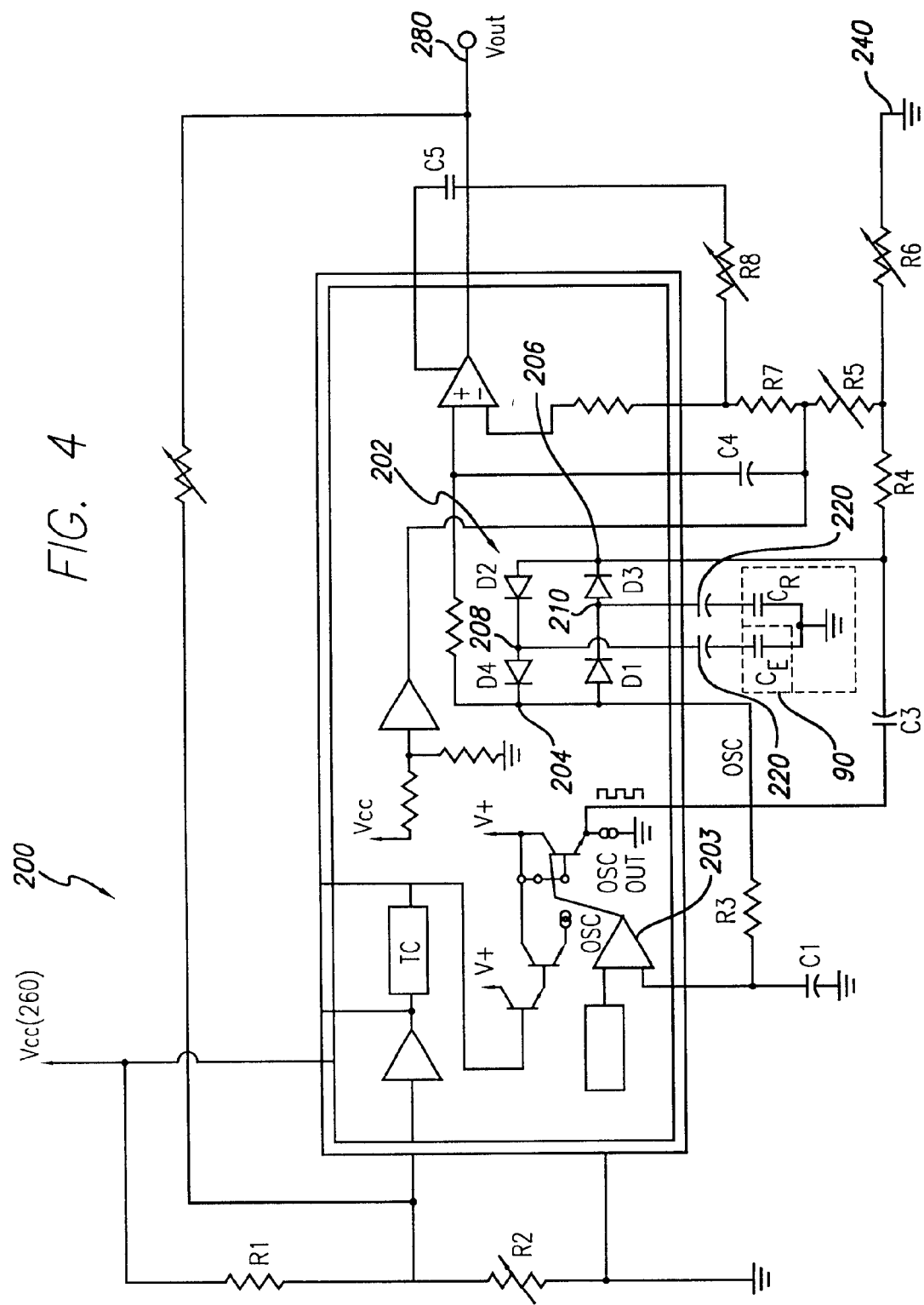
FIG. 4 is a detailed electrical circuit schematic of the capacitive oil deterioration and level sensor showing the isolating capacitors.

FIG. 4 (a duplicate circuit of FIG. 4 from U.S. Pat. No. 5,233,875) is an electrical schematic of circuitry 200 within the sensor 2 for generating an indication of engine oil dielectric constant and, more particularly, the oil deterioration output signal designated as ($V_{out}$) 280. For the purpose of simplification, the operating supply voltage ($V_{cc}$) 260 and a ground (GND) 240 are generally shown as being provided to the hybrid 30. As may be readily appreciated, the dashed-line boundary 90 of the hybrid 30 may be adjusted as circuit elements are either added to or relocated externally from the hybrid 30.

Generally, a capacitive transducer must be excited by an alternating current (AC) carrier voltage. Demodulating electronics are also needed to generate a direct current (DC)

output. Accordingly, the circuitry 200 includes a diode-quad circuit 202 which is excited by an AC carrier voltage provided by an oscillator (OSC) 203. The diode-quad circuit 202 further includes diodes D1, D2, D3 and D4 arranged to form nodes 204, 206, 208, 210. More specifically, the anode of D1 and the cathode of D4 are electrically connected at the node 204, the anode of D2 and the cathode of D3 are electrically connected at the node 206, the cathode of D2 and the anode of D4 are electrically connected at the node 208, and the cathode of D1 and the anode of D3 are electrically connected at the node 210.

The oil deterioration output signal (VOUT) is generated by the circuitry 200 and is described by the following formula:

$$V_{OUT} \propto (C_\epsilon - C_\Gamma)/(C_\epsilon + C_\Gamma)$$

The oil deterioration and level sensor capacitor ($C_\epsilon$) is electrically connected across the node 208 and GND. The reference capacitor ($C_\Gamma$) is electrically connected across the node 210 and GND. Since the capacitor $C_\epsilon$ is not included within the hybrid 30, it is shown inside the dashed-line outlining the hybrid 30.

Furthermore, isolating capacitors 220 are used to eliminate unwanted flow of direct current between the electrodes formed by 6" and 4', which can adversely affect the measurements from the sensor. The isolating capacitors have a magnitude at least several times greater than the capacitance of the variable and the reference capacitor. Preferably two isolating capacitors are used, one in series with each of the variable and reference capacitors on either side thereof. However, in some cases a single isolating capacitor between a common output point of the variable and fixed capacitors and ground may be effective.

Figure 2:
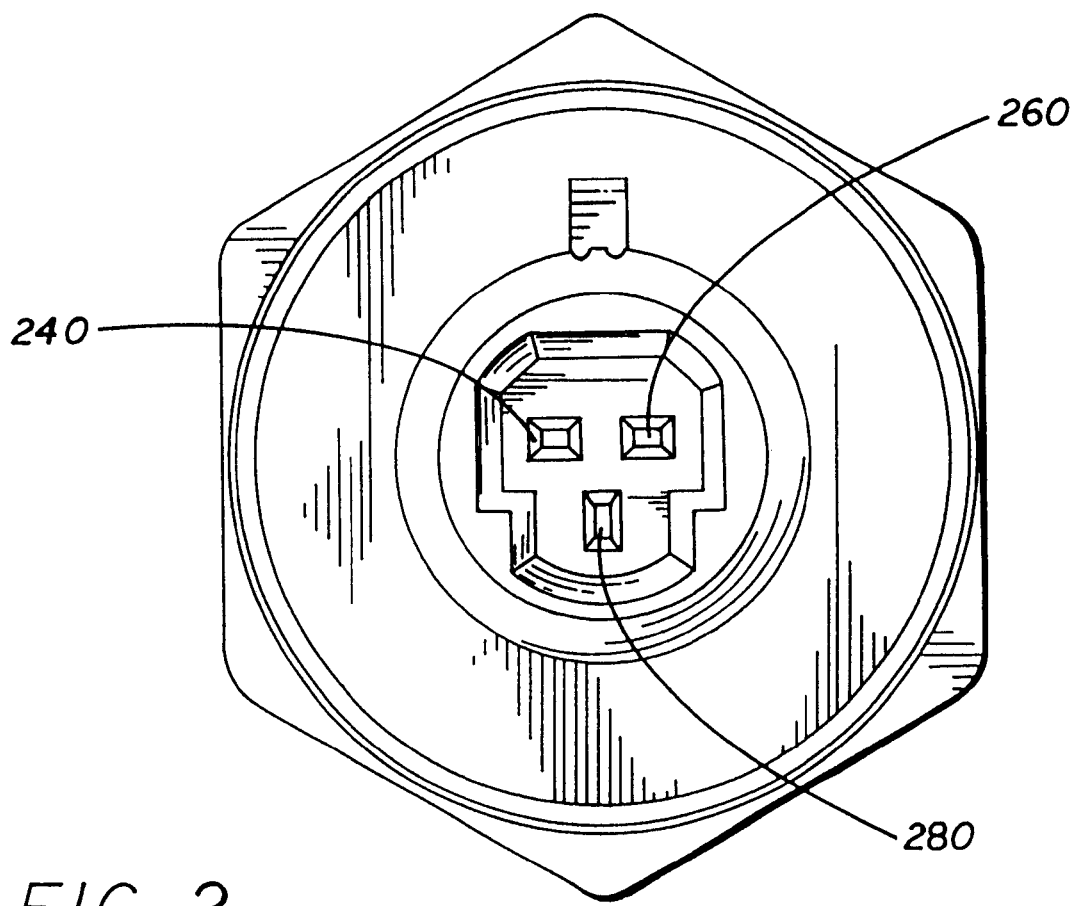
FIG. 2 is a rear view as seen from the connector end of the sensor assembly.

With reference to FIG. 3, the bottom view 50 depicts the electrical connector interface, and is shown in FIG. 2. The leads corresponding to ($V_{cc}$) 260, ($V_{out}$) 280, and (GND) 240 are shown.

The oil deterioration and level reference capacitor ($C_\Gamma$) is used to minimize the differences between the respective dielectric breakdown characteristics of various motor oil formulations.

After the motor oil begins to break down, the respective capacitances of $C_\epsilon$ and $C_\Gamma$, both change, with $C_\epsilon$ being more sensitive to changes in the dielectric constant of the motor oil than $C_\Gamma$.

An important benefit of the capacitor geometry of the present invention is the cost reduction that results from eliminating the gold plating of ceramic electrodes. The cylindrical electrodes can now be made out of aluminum with an anodized treatment to prevent shorts with the ground tube by oils with high metal particle content. A Teflon-based coating can also be used, with the additional benefit of discouraging soot adhesion to the surface of the electrodes. Finally, the gap between electrodes can now be increased while still obtaining large capacitance values since the area in contact with the oil is much larger. A preferred gap is 30 mils. Such a gap facilitates oil flow and ensures that all the oil will be renewed during oil change. The gap can be varied in response to the particular requirements of different sensor designs.

In conclusion, it is to be understood that the foregoing detailed description and the accompanying drawings illustrate the principles of the invention. However, various changes and modifications may be employed without departing from the spirit and scope of the invention. Thus by way of example, and not of limitation, the electrodes could be rectangular or of some other arbitrary shape and form, instead of being cylindrical. In addition, the shielding could be accomplished by a conductive screen secured to the outer end of an open outer electrode 6'. Accordingly, the present invention is not limited to the specific form shown in the drawings and described in detail hereinabove.

What is claimed is:

1. A reliable capacitive fluid deterioration and level sensing system comprising:

a housing member comprising of an outer conductive shielding member, said shielding member having an inner surface defining a ground electrode, wherein the conductive shielding member precludes interference by adjacent metallic structures, said shielding member having at least one inlet port for a fluid, the housing member further having a threaded outer surface adapted to be threaded to a fluid container;

a conductive inner member with an outer surface defining a measuring electrode, said inner member being secured within said housing member and spaced from the shielding member by an insulating material to allow the fluid from the inlet port to occupy said space, such that said ground electrode and said measuring electrode define a fluid deterioration and level sensor variable capacitor;

said outer conductive shielding member at least partially extending over the outer end of said conductive inner member;

said shielding member substantially enclosing said conductive inner member and extending over the greater portion of and more than half of the combined areas of said measuring electrode and the gap between electrodes, both as viewed from the sides and as viewed from the outer end of said conductive inner member;

an electrical connector structure adapted to provide an electrical interface; and electronics positioned within said housing member, said electronics being electrically connected to said fluid deterioration and level sensor capacitor, and said electrical connector structure, said electronics being adapted to generate a fluid deterioration output signal and a fluid level output signal employing said fluid deterioration and level sensor capacitor, and to provide said signals to the electrical connector structure.

2. The system according to claim 1, wherein the fluid container is an oil pan in an internal combustion engine.

3. The system according to claim 1, wherein said shielding member is cylindrical.

4. The system according to claim 1, wherein said inner member is cylindrical.

5. The system according to claim 1, wherein the space between shielding member and inner member is cylindrical.

6. The system according to claim 1, wherein the inner member is a metallic member.

7. The system according to claim 1, wherein the electronics provide an analog output signal.

8. The system according to claim 1, wherein the electronics include at least one isolating capacitor for eliminating a flow of direct current between the electrodes.

9. The system according to claim 8, wherein the isolating capacitor is in series with at least one capacitor.

10. The system according to claim 1, wherein the electronics have two separate isolating capacitors for eliminating a flow of direct current between the electrodes, a first isolating capacitor in series with a reference capacitor, and a second isolating capacitor in series with the variable capacitor.

11. A reliable capacitive fluid deterioration and level sensing assembly comprising:

a housing member having a threaded outer surface adapted to be threaded to a fluid container;

an outer conductive cylindrical member secured to said housing member, said outer conductive cylindrical member defining a ground electrode, and further having at least one inlet port for a fluid;

an inner conductive cylindrical member defining a measuring electrode and secured within said housing member, the inner cylindrical member being spaced from the outer cylindrical member to allow the fluid to occupy said space, such that the ground electrode and the measuring electrode define a fluid deterioration and level sensor capacitor; and a shielding structure secured to said outer conductive cylindrical member to substantially enclose the inner electrode except for fluid flow openings, and extending over substantially more than half of the area of the inner electrode and the gap between electrodes at the sides and at the outer end of said inner electrode, said cylindrical members having a control axis and said shielding structure extending inwardly over one end of said measuring electrode toward said axis, wherein the shielding structure precludes interference by adjacent metallic structures, thereby permitting reliable operation of the fluid deterioration and level sensor capacitor.

12. The assembly according to claim 11, wherein the housing member is made of metal.

13. The assembly according to claim 11, wherein the fluid container is an oil pan in an internal combustion engine.

14. The assembly according to claim 11, wherein said space between the electrodes is cylindrical.

15. The assembly according to claim 11, wherein the inner member is made of metal.

16. The assembly according to claim 11, wherein the shielding structure is cylindrical.

17. A reliable capacitive fluid deterioration and level sensing assembly comprising:

a housing member having a threaded outer surface adapted to be threaded to a fluid container;

an outer conductive member secured to said housing member, said outer conductive member defining a ground electrode, and further having at least one inlet port for a fluid;

an inner conductive member defining a measuring electrode and secured within said housing member, the inner member being spaced from the outer member to allow the fluid to occupy said space, such that the ground electrode and the measuring electrode define a fluid deterioration and level sensor capacitor; and a shielding structure secured to said outer conductive member to substantially enclose the inner electrode except for fluid flow openings, and extending over substantially more than half of the area of the inner electrode and the gap between electrodes as viewed from the sides and as viewed from the outer end of said inner electrode, wherein the shielding structure precludes interference by adjacent metallic structures, thereby permitting reliable operation of the fluid deterioration and level sensor capacitor.

18. The assembly according to claim 17, wherein said outer member is cylindrical.

19. The assembly according to claim 17, wherein said inner member is cylindrical.

20. The assembly according to claim 17, wherein the shielding structure is cylindrical.

\* \* \* \* \*